(12) United States Patent
Markworth et al.

(10) Patent No.: US 8,062,374 B2
(45) Date of Patent: Nov. 22, 2011

(54) COMPLIANT INTERBODY FUSION DEVICE WITH DEPLOYABLE BONE ANCHORS

(75) Inventors: Aaron D. Markworth, Saddle Brook, NJ (US); YoungHoon Oh, Montville, NJ (US); Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 469 days.

(21) Appl. No.: 12/326,079

(22) Filed: Dec. 1, 2008

(65) Prior Publication Data

US 2010/0137988 A1 Jun. 3, 2010

(51) Int. Cl.
*A61F 2/44* (2006.01)

(52) U.S. Cl. .................... 623/17.16; 623/17.11

(58) Field of Classification Search ..... 623/17.11–17.16
See application file for complete search history.

(56) References Cited

U.S. PATENT DOCUMENTS

| | | | |
|---|---|---|---|
| 6,527,803 B1 * | 3/2003 | Crozet et al. | 623/17.11 |
| 6,981,975 B2 | 1/2006 | Michelson | |
| 7,879,099 B2 * | 2/2011 | Zipnick | 623/17.11 |
| 2005/0049590 A1 * | 3/2005 | Alleyne et al. | 606/61 |
| 2006/0224241 A1 | 10/2006 | Butler et al. | |
| 2006/0253201 A1 | 11/2006 | McLuen | |

* cited by examiner

*Primary Examiner* — Eduardo C Robert
*Assistant Examiner* — Ellen C Hammond
(74) *Attorney, Agent, or Firm* — Rahman LLC

(57) ABSTRACT

An interbody fusion implant with deployable bone anchors includes a support member, a monolithic body that accommodates the support member, and a longitudinal hole along a vertical length of the support member. The support member includes a first end and a second end. The second end includes two flanges. The flanges are configured to dig into an endplate of a vertebral body. The flanges of the support member provide a location fixation on an implantation of the interbody fusion implant into the vertebral body. The support member may also include at least one of a clip shaped support member and an I-shaped support member. The I-shaped support member may allow a rigidity and a support in flexion-extension through a living-hinge positioned in a middle of the I-shaped support member. The longitudinal hole sustains loads imported on the interbody fusion implant and allows the interbody fusion implant to flex freely.

11 Claims, 11 Drawing Sheets

COMPLIANT INTERBODY FUSION DEVICE WITH DEPLOYABLE BONE ANCHORS

BACKGROUND

1. Technical Field

The embodiments herein generally relate to spinal stabilization devices, and more particularly to a compliant interbody fusion device with deployable bone anchors.

2. Description of the Related Art

Conventional spinal fusion implants typically having projections that can be deployed after the implant has been inserted into the disc space and are used to stabilize the human spine. A problem with the conventional spinal fusion implants is that they are static in size. This poses various problems with their use and/or implantation. As a result, nerves may become pinched, causing pain that radiates into other parts of the body and instability in the vertebrae.

To overcome this, spinal decompression and fusion procedures can be augmented with bone or implants being inserted between the vertebral bodies and held in place with pedicle screws. This disrupts the normal biomechanics of the spine while correcting the instability. Fusion, while correcting the instability, can also cause adjacent disc disease. Also, generally the conventional interbody designs are non-complaint or do not have deployable bone anchors that can be opened after insertion to aid ease of implantation.

These standard devices are also more prone to subsidence and may contribute to adjacent disc disease. Moreover, these devices generally do not help in restoring the normal biomechanics of the thoraco-lumbar spine. In conjunction with a dynamic rod/screw system or stand-alone, the device may not reduce the chances of adjacent disk disease.

SUMMARY

In view of the foregoing, an embodiment herein provides an interbody fusion implant with deployable bone anchors including a support member having a first end and a second end, the second end including two flanges, the flanges are configured to dig into an endplate of a vertebral body. The interbody fusion implant further includes a monolithic body that accommodates the support member, and a longitudinal hole along a vertical length of the support member. The longitudinal hole sustains loads imported on the interbody fusion implant and allows the interbody fusion implant to flex freely.

The support member includes at least one of a clip shaped support member and an I-shaped support member. The flanges of the support member may provide a location fixation on an implantation of the interbody fusion implant into the vertebral body. The I-shaped support member allows rigidity and a support in flexion-extension through a living-hinge positioned in a middle of the I-shaped support member. The I-shaped support member is cut in a front and a side plane to enable two degrees of freedom and to bend in at least one of a sagital and a transverse plane.

To overcome this, spinal decompression and fusion procedures can be augmented with bone or implants being inserted between the vertebral bodies and held in place with pedicle screws. This disrupts the normal biomechanics of the spine while correcting the instability. Fusion, while correcting the instability, can also cause adjacent disc disease. Also, generally the conventional interbody designs are non-compliant or do not have deployable bone anchors that can be opened after insertion to aid ease of implantation.

Another embodiment provides an apparatus to stabilize a human spine. The apparatus includes a compliant monolithic interbody fusion implant including at least one support member having at least one rod that is rotated with a driving instrument, a plurality of spikes attached to the rod, a monolithic compliant body that accommodates the rod and the spikes, at least one window molded in the monolithic compliant body, and an inserter tool that inserts the compliant monolithic interbody fusion implant into the human spine.

Yet another embodiment provides an interbody fusion assembly for attachment to endplates of vertebral bodies. The interbody fusion assembly includes a tube including at least one hole, the tube including a camshaft, a plurality of cams coupled to the camshaft, and a plurality of free moving spikes coupled to the cams along a perpendicular axis to the camshaft, and a compliant monolithic body that accommodates the tube. The free moving spikes are positioned in a vertical orientation and set within the tube. The plurality of cams force the free moving spikes upward into the endplates of the vertebral bodies upon rotation of the camshaft. The free moving spikes may cut at least partially through the compliant monolithic body.

The free moving spikes penetrate the endplates to fix the compliant monolithic interbody fusion assembly in place upon rotation of the camshaft. A plurality of holes may be molded into the compliant monolithic body to allow passage of the free moving spikes. A cephalad and a caudal surface of the compliant monolithic body is molded with surface finishes to provide fixation with the endplates. The surface finishes include at least one of teeth, geometry, and serrations.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1A:
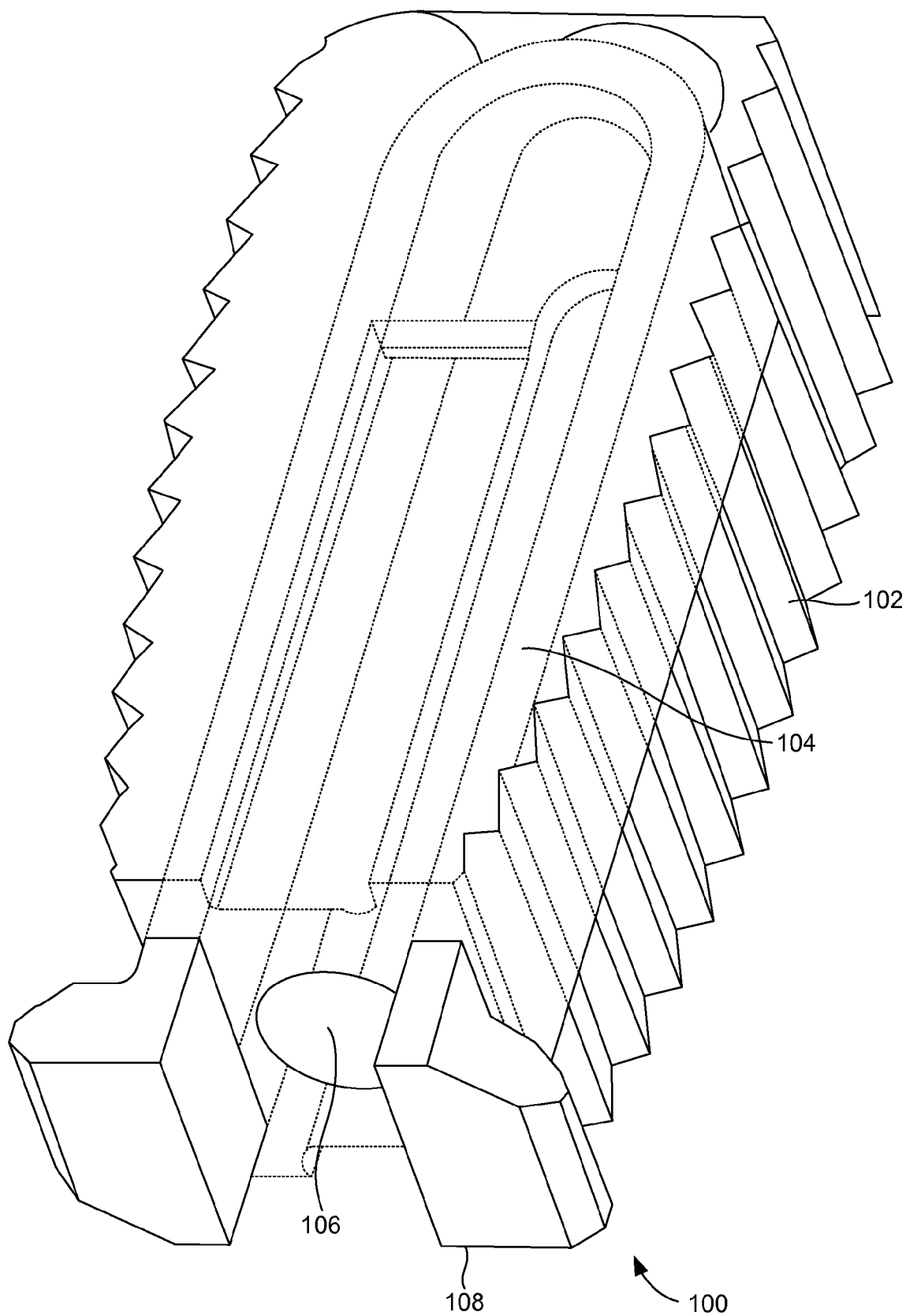
FIGS. 1A and 1B illustrate perspective views of a compliant monolithic spinal fusion implant according to a first embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a compliant material monolithic spinal fusion device for spinal stabilization. The embodiments herein provide an I-shaped support member of a spinal fusion implant that allows more rigidity and support through the middle of the device and act as a living-hinge in flexion-extension, enables two degrees of freedom, acting as a joint that can bend in both the sagital and transverse planes.

The compliant material monolithic spinal fusion device aids in restoring the normal biomechanics of the thoracolumbar spine. In conjunction with a dynamic rod/screw system or stand-alone, the device reduces the chances of adjacent disk disease. Referring now to the drawings and more particularly to FIGS. 1A through 5C where similar reference characters denote corresponding features consistently throughout the figures, there are shown preferred embodiments.

Figure 1B:
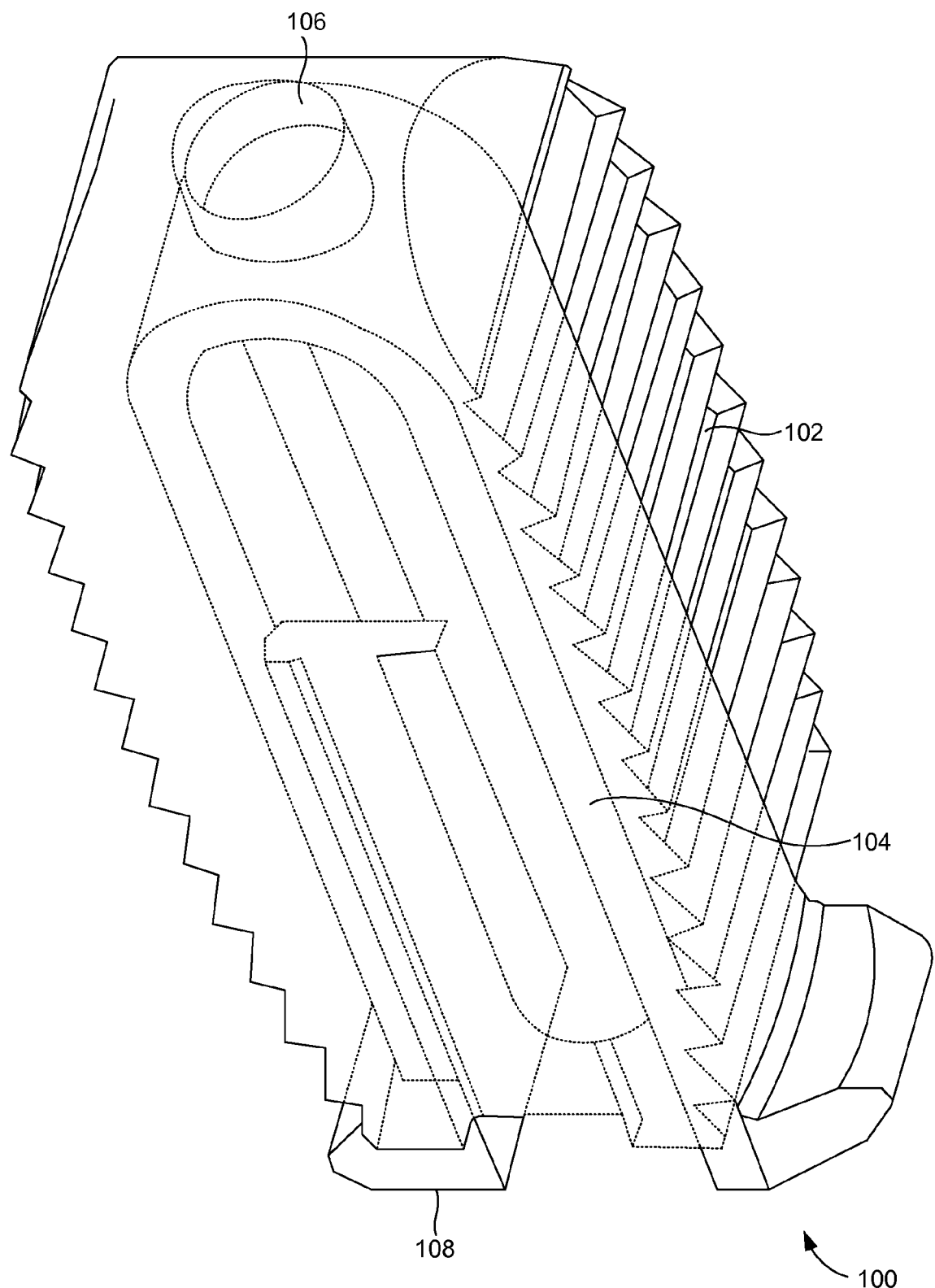

FIGS. 1A and 1B illustrate a perspective view of a compliant monolithic spinal fusion implant 100 according to a first embodiment herein. With reference to FIGS. 1A and 1B, the compliant monolithic spinal fusion implant 100 includes a compliant monolithic body 102, a support member 104, a longitudinal hole 106 along the vertical length of the support member 104, and flanges 108 located near the opening of the hole 106. The compliant monolithic spinal fusion implant 100 may be inserted anteriorly, posteriorly, or transforaminal in between vertebral bodies of the spine.

The longitudinal hole 106 along the vertical length of the clip shaped support member 104 enables the support member 104 to sustain a heavy load and flex freely. A cephalad and a caudal surface of the compliant monolithic spinal fusion implant 100 may be molded with a surface finish (e.g., teeth, geometry, or serrations) to provide an additional fixation with endplates (not shown). In one embodiment, the support member 104 is embodied as a clip shaped support member. In another embodiment, the geometry of the support member 104 provides flexibility and can be squeezed shut for a minimal profile during an insertion and ease of attachment to an insertion tool (not shown).

When the insertion tool (not shown) is removed, the support member 104 may spring open to support the vertebral bodies. The flanges 108 on the end of the support member 104 may dig into the endplates to provide a location fixation. The compliant monolithic spinal fusion implant 100 may be inserted or impacted by means of the inserter tool (not shown).

In a preferred mode, the inserter tool (not shown) includes a shaft of an adequate length. One end of the inserter tool (not shown) may include a protrusion attached to the compliant monolithic spinal fusion implant 100 via a snap fitting around the flanges 108 of the support member 104. The opposite end of the inserter tool (not shown) may include a handle with an impact surface. When the compliant monolithic spinal fusion implant 100 is loaded, the inserter tool (not shown) is lightly impacted, the compliant monolithic spinal fusion implant 100 may get wedged between the vertebral bodies, slightly decompress them and provide support surfaces for proper biomechanical movement of the spine.

Figure 2A:
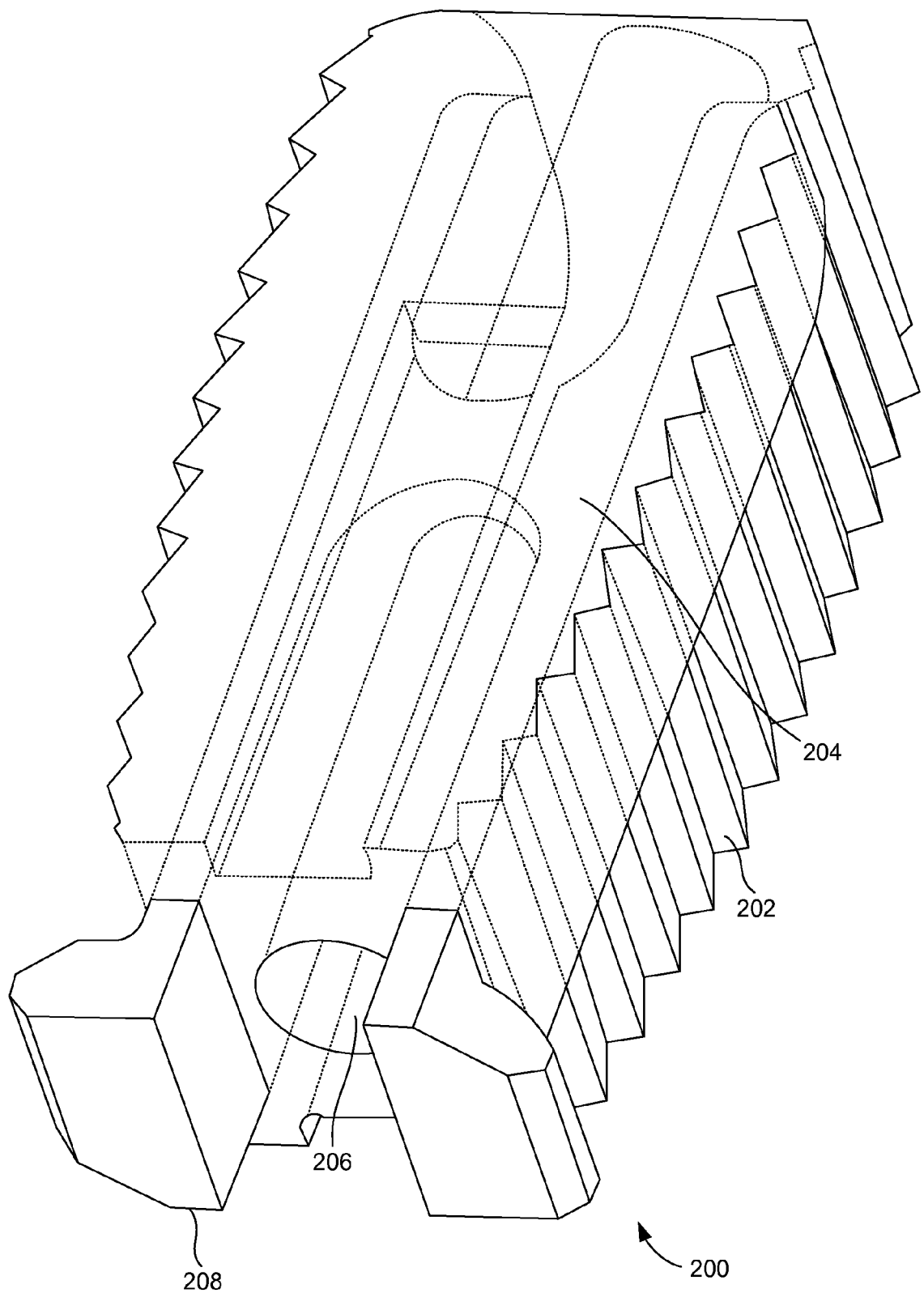
FIGS. 2A and 2B illustrate perspective views of a compliant monolithic spinal fusion implant according to a second embodiment herein.
Figure 2B:
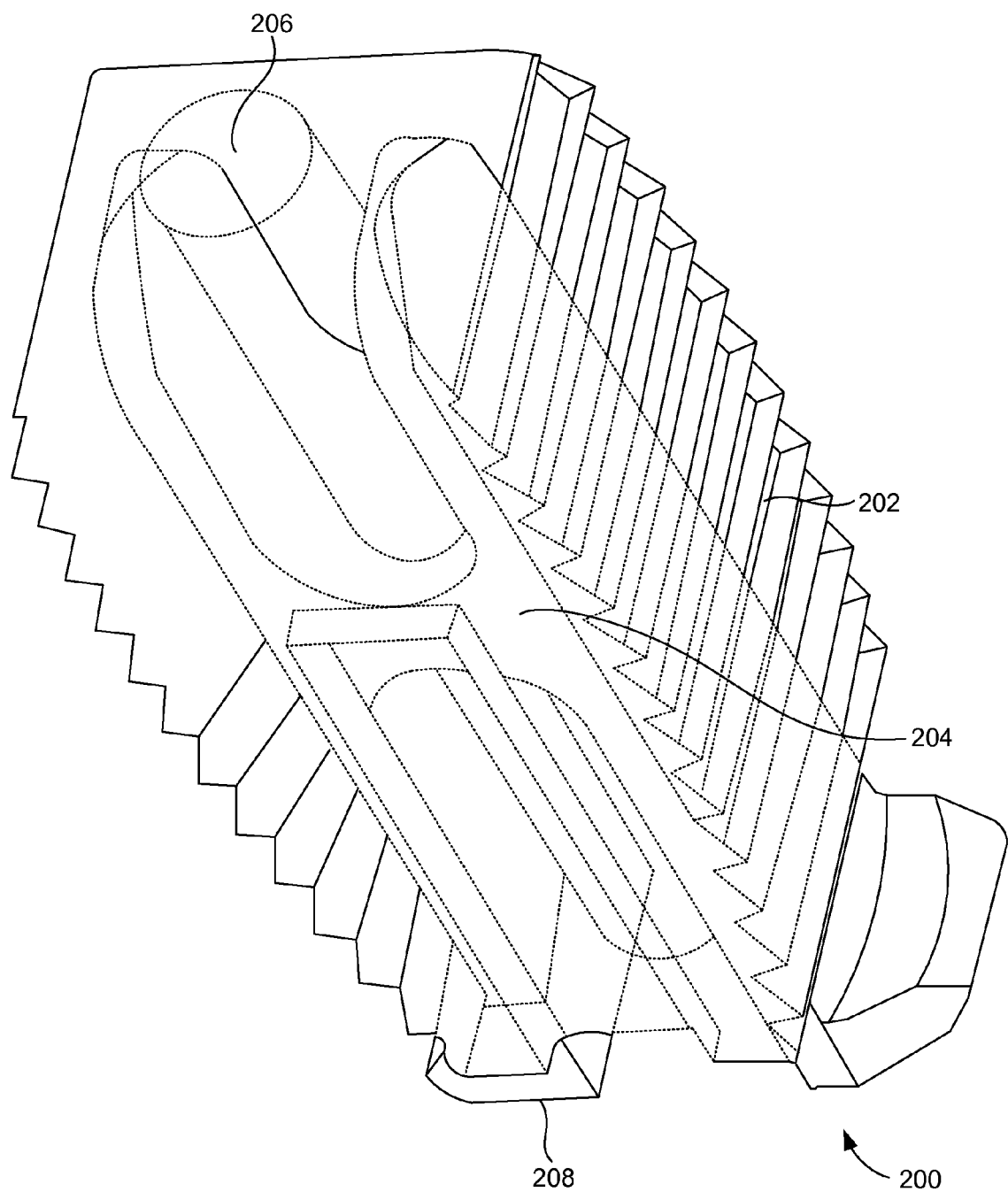

FIGS. 2A and 2B illustrate a perspective view of a compliant monolithic spinal fusion implant 200 according to a second embodiment herein. The compliant monolithic spinal fusion implant 200 includes a compliant monolithic body 202, a support member 204, a longitudinal hole 206 along the vertical length of the I-shaped support member 204, and flanges 208. The support member 204 may allow more rigidity and support through the middle of the support member 204 which acts as a living-hinge in flexion-extension.

In one embodiment, the support member 204 is an I-shaped support member. The support member 204 may also be cut in both the front and side planes to allow two degrees of freedom, acting as a joint that can bend in both the sagital and transverse planes. The longitudinal hole 206 along the vertical length of the support member 204 may enable the support member 204 to sustain a heavy load and flex freely. The flanges 208 on the end of the support member 204 may dig into endplates (not shown) to provide a location fixation.

Figure 3A:
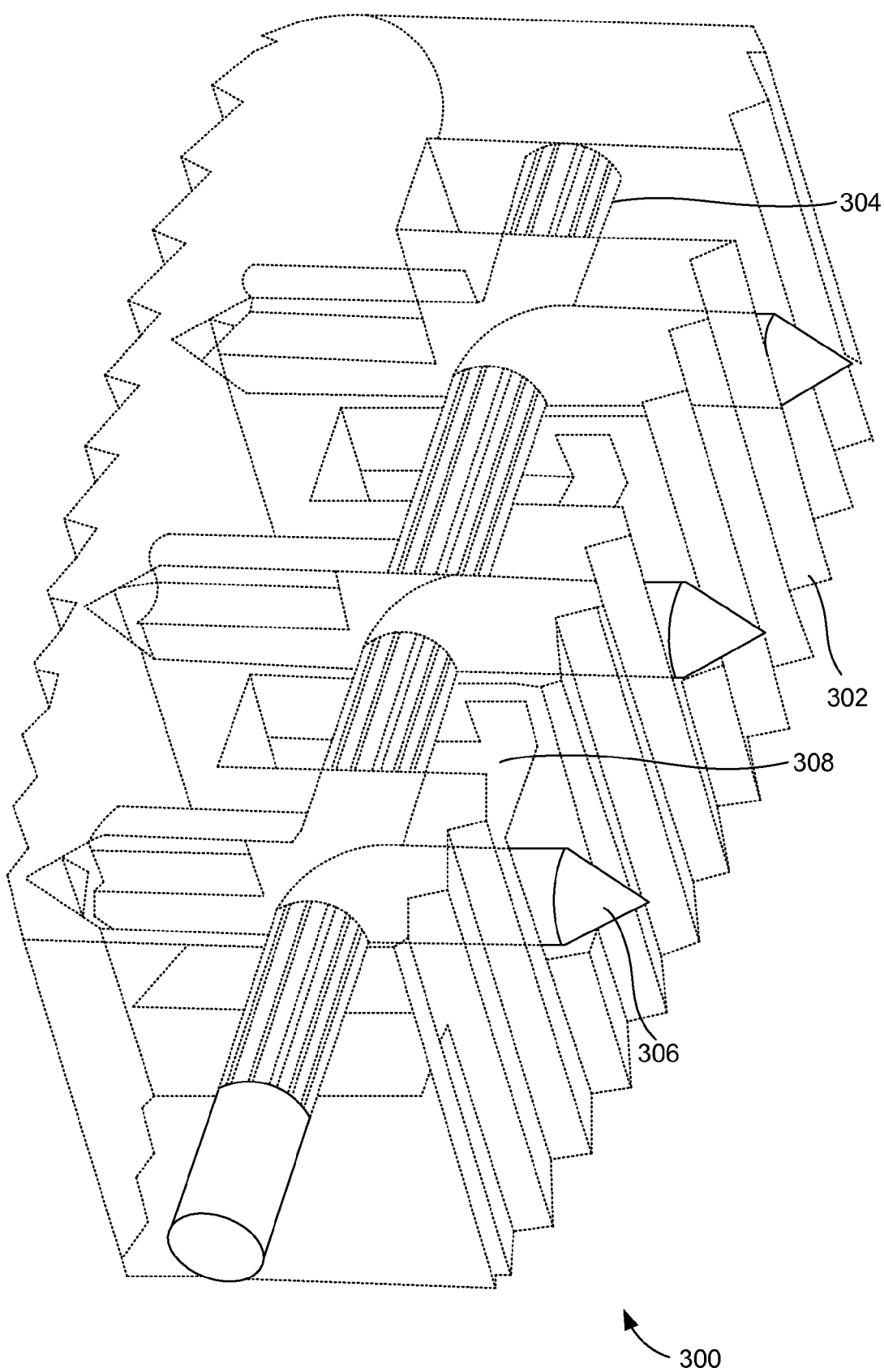
FIGS. 3A and 3B illustrate perspective views of a compliant monolithic spinal fusion implant according to a third embodiment herein.
Figure 3B:
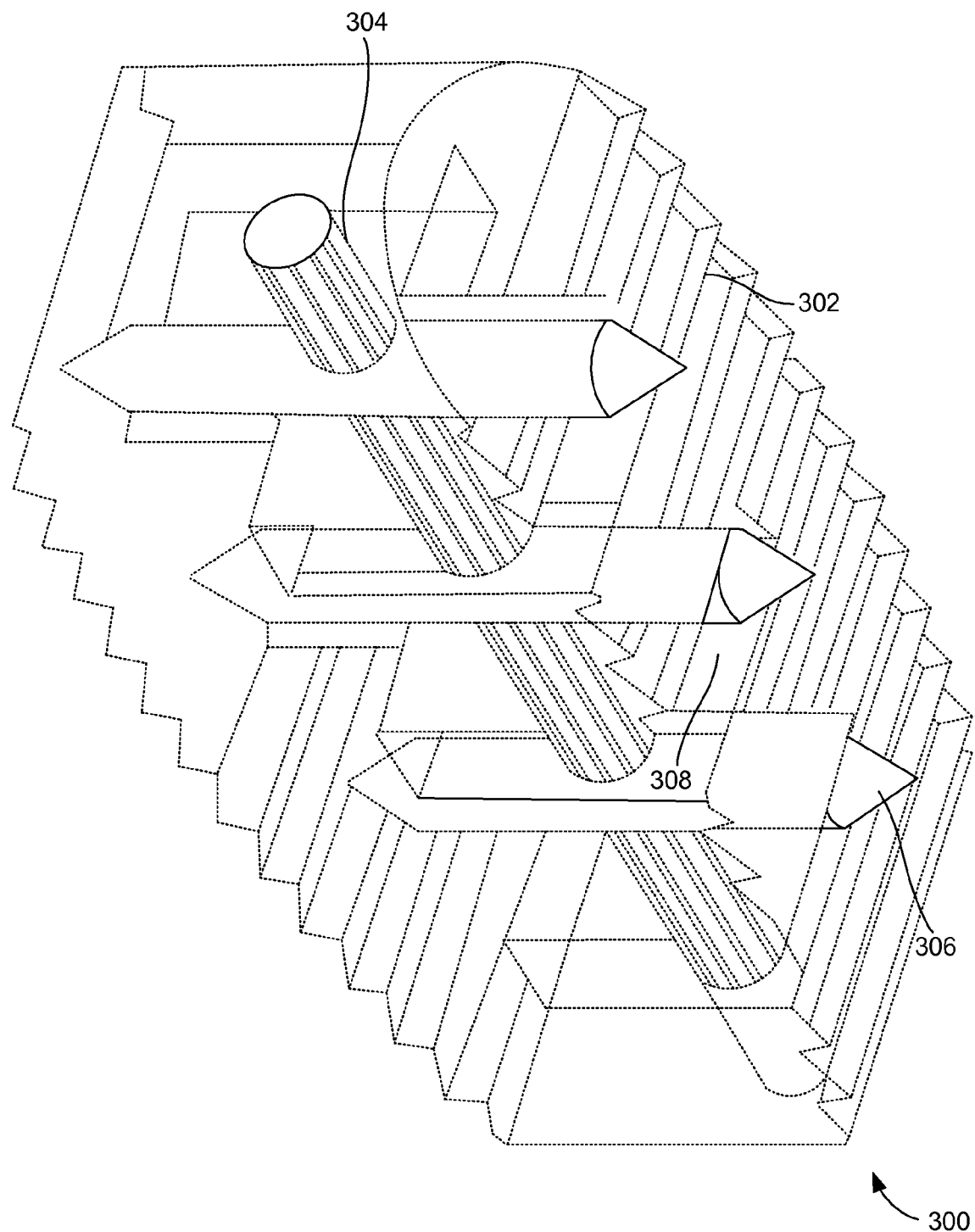

FIGS. 3A and 3B illustrate a perspective view of a compliant monolithic spinal fusion implant 300 according to a third embodiment herein. The compliant monolithic spinal fusion implant 300 includes a compliant monolithic body 302, a rod 304 longitude to the compliant monolithic body 302 with a plurality of symmetric spikes 306, and windows 308. The rod 304 is insert-molded in the compliant monolithic body 302. The spikes 306 are attached to the rod 304 perpendicular to the main axis of the rod 304.

The windows 308 are molded in the compliant monolithic body 302 to enable the rod 304 to rotate from a horizontal to a vertical configuration. In the vertical configuration, the spikes 306 penetrate the end plates (not shown) to fix the compliant monolithic body 302 in place. The rod 304 may be rotated with an appropriate driving instrument (not shown).

Figure 4A:
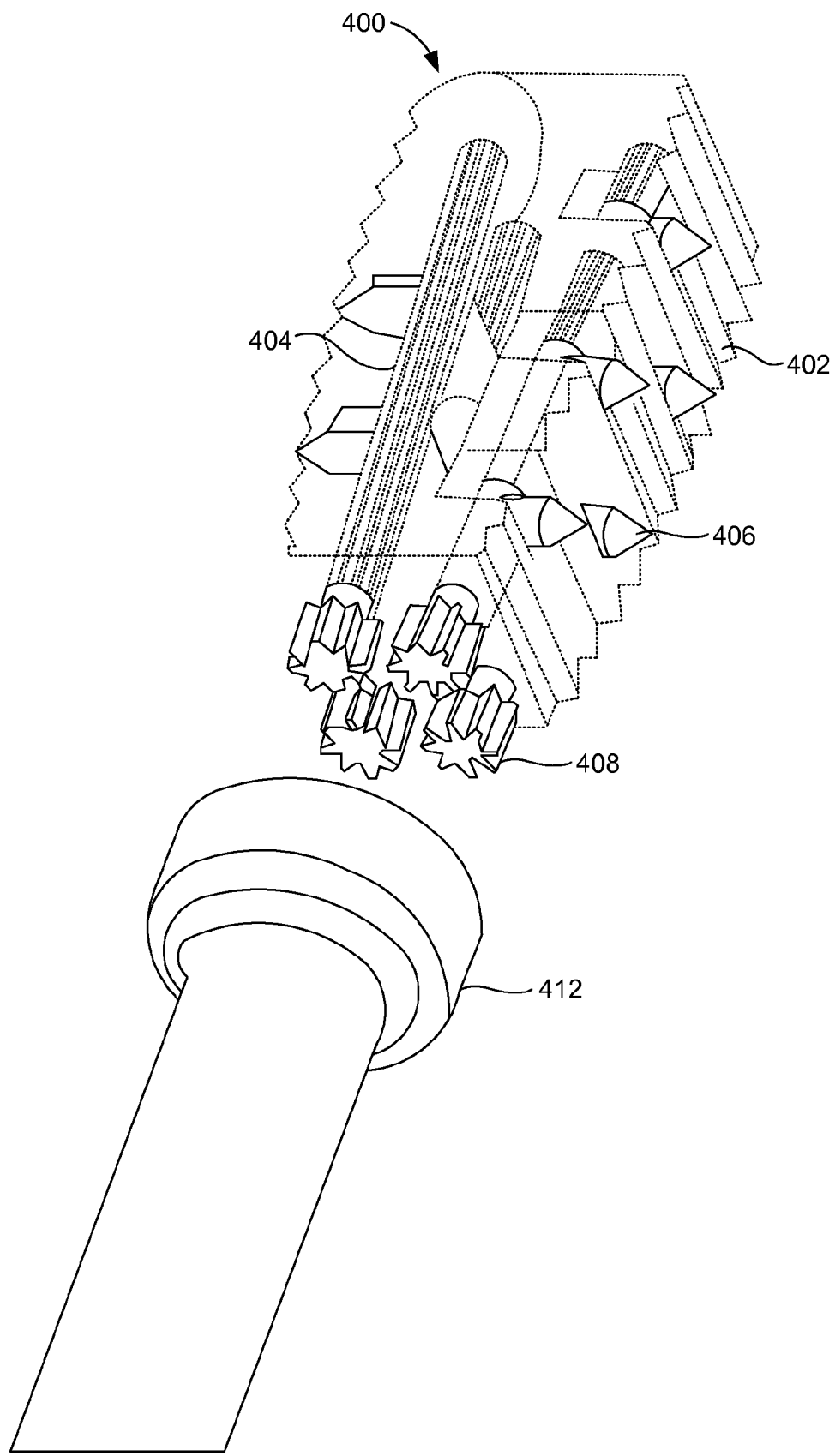
FIGS. 4A and 4B illustrate perspective views of a compliant monolithic spinal fusion implant and an inserter tool according to a fourth embodiment herein.
Figure 4B:
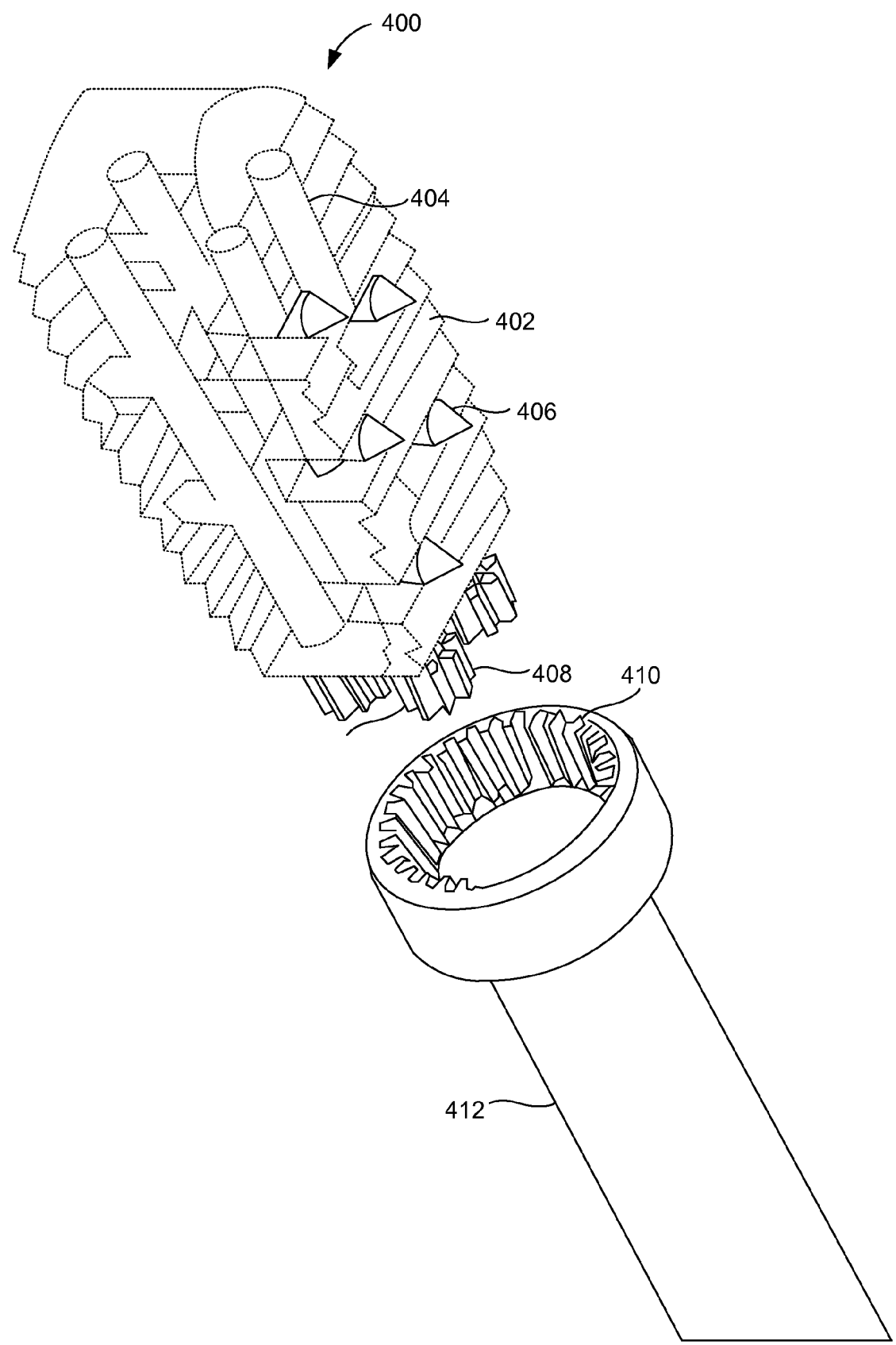

FIGS. 4A and 4B illustrate a perspective view of a compliant monolithic spinal fusion implant 400 and an inserter tool 412 according to a fourth embodiment herein. The compliant monolithic spinal fusion implant 400 includes a compliant monolithic body 402 and a plurality (e.g., four) separate rods 404. Each of the rods 404 includes one set of spikes 406 and gears 408. The rods 404 are insert-molded into the compliant monolithic body 402 and have the ability to rotate from a horizontal to a vertical configuration.

The rods 404 are positioned within the compliant monolithic body 402 so as to have a cephalad and a caudal set. The spikes 406 are attached to the rod 404 perpendicular to the main axis of the rods 404. The gears 408 are positioned along the main, longitudinal axis of the rods 404. The gears 408 at the proximal end of the rods 404 enables the ability to drive and rotate the rods 404 from a horizontal to a vertical position. In one embodiment, the rods 404 are positioned and the gears 408 timed to each other so that a single driving instrument 412 with female beveled gears 410 may deploy them simultaneously with one turn motion. The inserter tool 412 is used to insert the compliant monolithic spinal fusion implant 400 into the vertebral bodies of the spine.

One end of the inserter tool 412 has a protrusion 410 to receive the gears 408 of the rods 404 attached to the compliant monolithic body 402. The opposite end of the inserter tool 412 has a handle with an impact surface. When the compliant monolithic spinal fusion implant 400 is loaded in the inserter tool 412 and inserted, the compliant monolithic spinal fusion implant 400 gets wedged between the vertebral bodies, slightly decompress them and provide support surfaces for proper biomechanical movement of the spine.

Figure 5A:
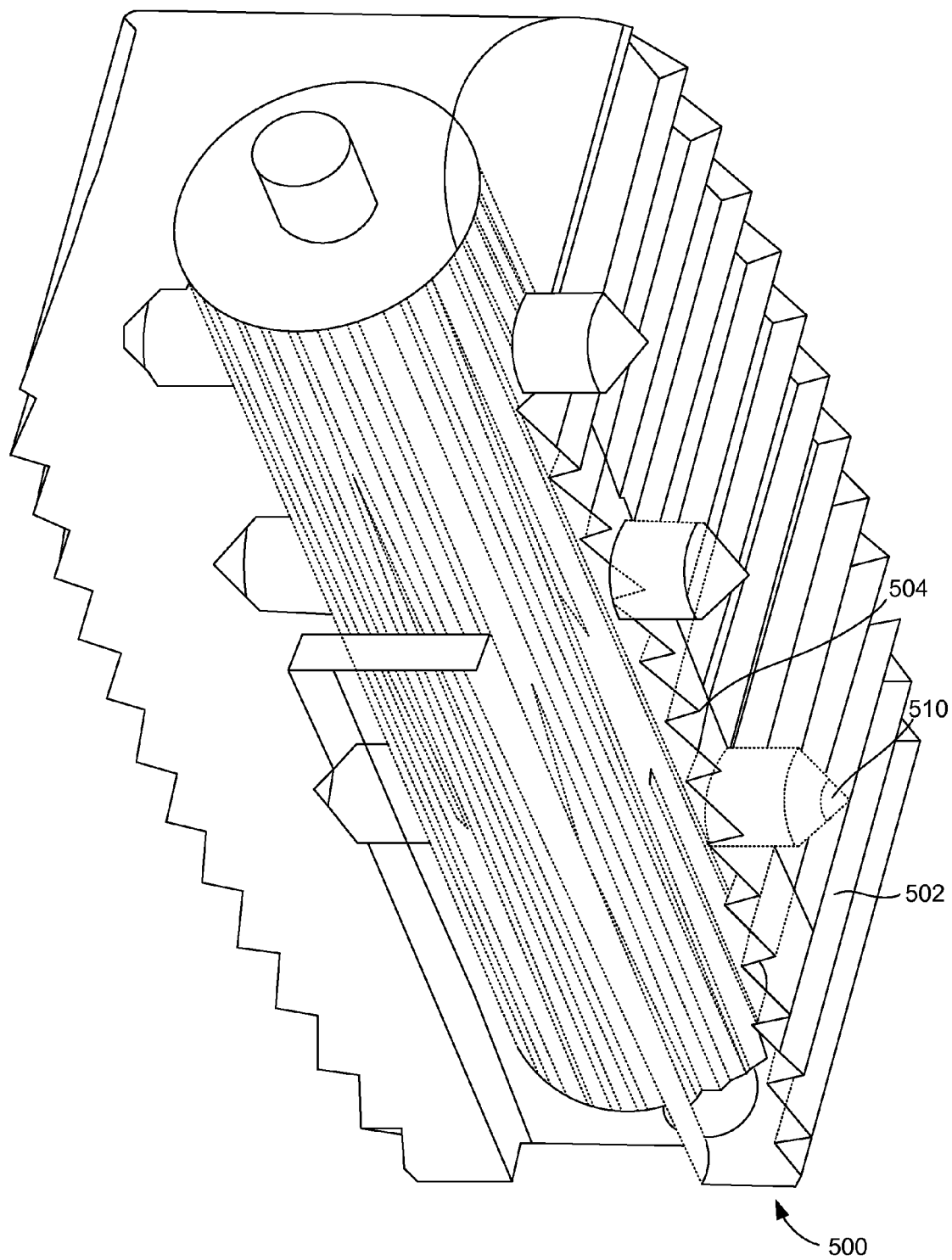
FIGS. 5A and 5B illustrate perspective views of a compliant monolithic spinal fusion implant according to a fifth embodiment herein.
Figure 5B:
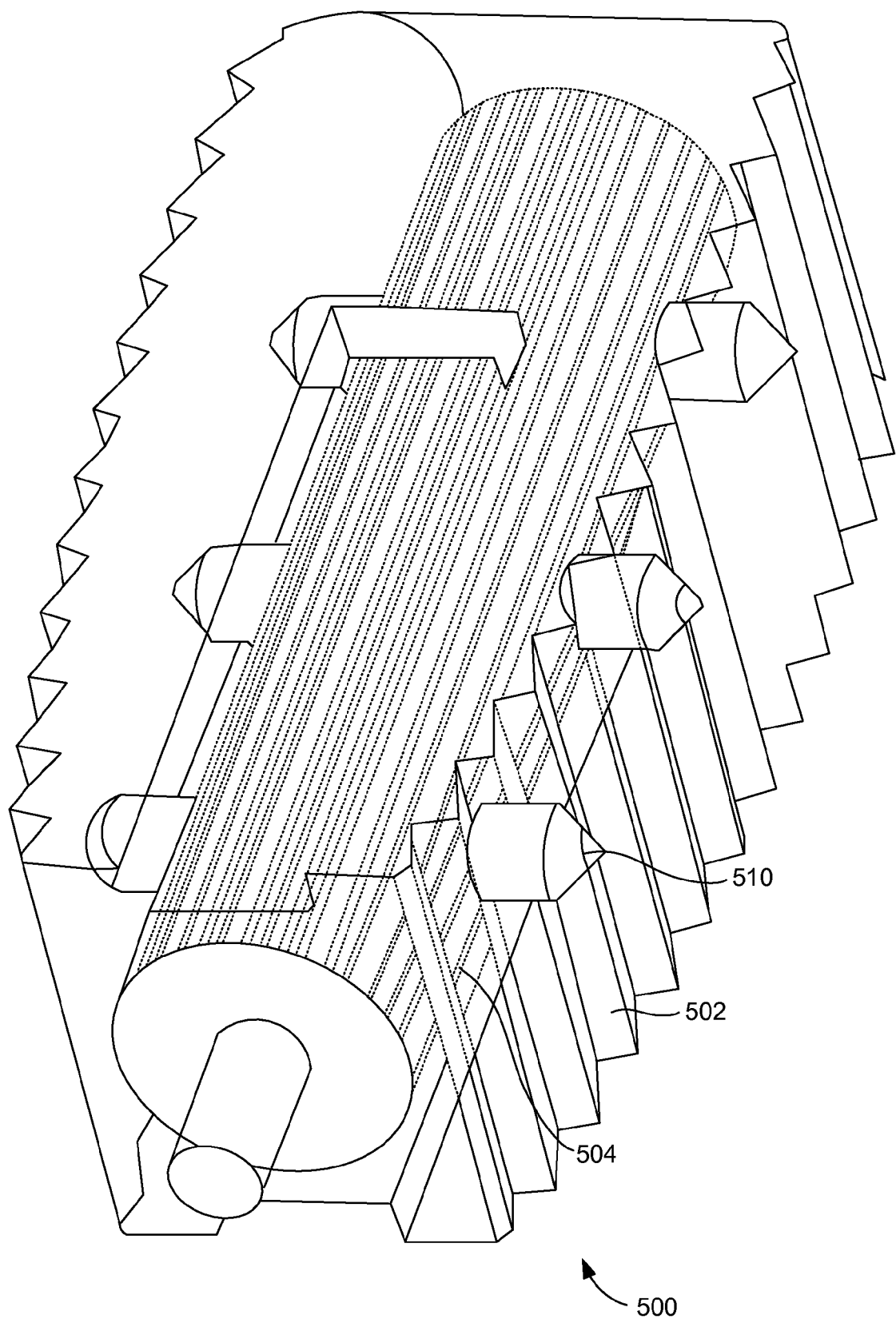
Figure 5C:
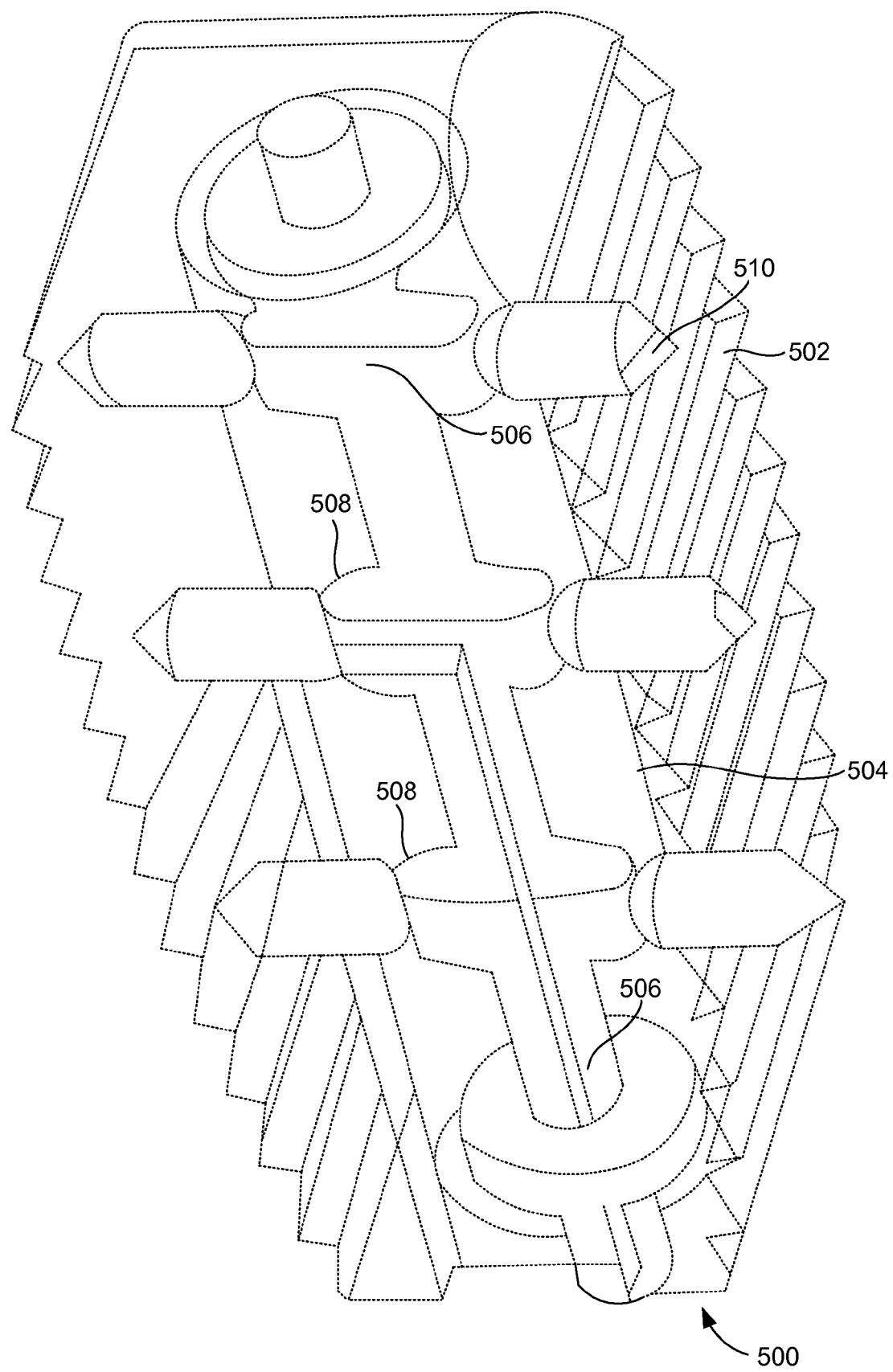
FIG. 5C illustrates a sectional view of a compliant monolithic spinal fusion implant according to a fifth embodiment herein.

FIGS. 5A and 5B illustrate a perspective view of a compliant monolithic spinal fusion implant 500 according to a fifth embodiment herein. FIG. 5C illustrates a sectional view of a compliant monolithic spinal fusion implant 500 according to a fifth embodiment herein. The compliant monolithic spinal fusion implant 500 includes a compliant monolithic body 502, a tube 504, a camshaft 506, cams 508, and a plurality of free moving spikes 510. The cams 508 are attached to the camshaft 506.

The camshaft 506 and the spikes 510 are insert molded into the compliant monolithic body 502 and positioned in a vertical orientation and set within the tube 504 with holes. The tube 504 acts as housing for the camshaft 506. In one embodiment, when the camshaft 506 is rotated, the cams 508 force the spikes 510 upward into the endplates (not shown) of the vertebral bodies, fixing the compliant monolithic spinal fusion implant 500 in place. In another embodiment, the spikes 510 may have to cut their way through the compliant monolithic body 502 or there may be holes molded into the compliant monolithic body 502 to allow easier passage.

The embodiments herein provide a compliant material monolithic spinal fusion implant that may be inserted anteriorly, posteriorly, or transforaminal in between vertebral bodies of the spine. The design provides an optimal surface coverage while acting as a compliant interbody or disc. It is held in place by various embodiments of deployable bone anchors. The I-shaped support member 204 of FIG. 2 allows additional rigidity and support through the middle of the device and acts as a living-hinge in flexion-extension. The I-shaped support member 204 may also be cut in both the front and side planes to allow two degrees of freedom, acting as a joint that can bend in both the sagital and transverse planes.

The compliant material monolithic spinal fusion devices 100, 200, 300, 400, 500 are used in surgery to stabilize the human spine. They aid in restoring the normal biomechanics of the thoraco-lumbar spine. In conjunction with a dynamic rod/screw system or stand-alone, the devices 100, 200, 300, 400, 500 reduce the chances of adjacent disk disease. These devices 100, 200, 300, 400, 500 are an improvement over existing devices in terms of fixation to the endplates. The devices 100, 200, 300, 400, 500 are designed to work with any appropriate compliant implantable material and may utilize all the standard surgical tools that accompany such devices 100, 200, 300, 400, 500.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An interbody fusion assembly for attachment to endplates of vertebral bodies, said assembly comprising:
    a tube having at least one hole, said tube comprising:
        a camshaft;
        a plurality of cams coupled to said camshaft; and
        a plurality of free moving spikes coupled to said cams and positioned along a perpendicular axis to said camshaft; and
    a compliant monolithic body that accommodates said tube,
        wherein said plurality of cams force said free moving spikes upward upon rotation of said camshaft,
        wherein said free moving spikes cut at least partially through said compliant monolithic body, and
        wherein a cephalad and a caudal surface of said compliant monolithic body is molded with surface finishes to provide fixation with said endplates.

2. The interbody fusion assembly of claim 1, wherein said free moving spikes are positioned in a vertical orientation and set within said tube.

3. The interbody fusion assembly of claim 1, wherein said free moving spikes fix said compliant monolithic interbody fusion assembly in place upon rotation of said camshaft.

4. The interbody fusion assembly of claim 1, wherein said surface finishes comprise at least one of teeth, geometry, and serrations.

5. An interbody fusion assembly for attachment to endplates of vertebral bodies, said assembly comprising:
    a tube having at least one hole, said tube comprising:
        a camshaft;
        a plurality of cams coupled to said camshaft; and
        a plurality of free moving spikes coupled to said cams and positioned along a perpendicular axis to said camshaft; and
    a compliant monolithic body that accommodates said tube,
        wherein said plurality of cams force said free moving spikes upward upon rotation of said camshaft, and
        wherein said free moving spikes cut at least partially through said compliant monolithic body.

6. The interbody fusion assembly of claim 5, wherein said free moving spikes are positioned in a vertical orientation and set within said tube.

7. The interbody fusion assembly of claim 5, wherein said free moving spikes fix said compliant monolithic interbody fusion assembly in place upon rotation of said camshaft.

8. The interbody fusion assembly of claim 5, wherein a cephalad and a caudal surface of said compliant monolithic body is molded with surface finishes to provide fixation with said endplates, wherein said surface finishes comprise at least one of teeth, geometry, and serrations.

9. An interbody fusion assembly for attachment to endplates of vertebral bodies, said assembly comprising:
    a tube having at least one hole, said tube comprising:
        a camshaft;
        a plurality of cams coupled to said camshaft; and
        a plurality of free moving spikes coupled to said cams and positioned along a perpendicular axis to said camshaft; and
    a compliant monolithic body that accommodates said tube,
        wherein said plurality of cams force said free moving spikes upward upon rotation of said camshaft,
        wherein said free moving spikes cut at least partially through said compliant monolithic body, and
        wherein said free moving spikes fix said compliant monolithic interbody fusion assembly in place upon rotation of said camshaft.

10. The interbody fusion assembly of claim 9, wherein said free moving spikes are positioned in a vertical orientation and set within said tube.

11. The interbody fusion assembly of claim 9, wherein a cephalad and a caudal surface of said compliant monolithic body is molded with surface finishes to provide fixation with said endplates, wherein said surface finishes comprise at least one of teeth, geometry, and serrations.

* * * * *